United States Patent
Yamada

(10) Patent No.: US 9,919,856 B2
(45) Date of Patent: Mar. 20, 2018

(54) MICRONEEDLE-SHEET PACKAGING BODY AND METHOD OF MANUFACTURING THE SAME

(71) Applicant: NISSHA PRINTING CO., LTD., Kyoto-shi, Kyoto (JP)

(72) Inventor: Shinya Yamada, Kyoto (JP)

(73) Assignee: Nissha Co., Ltd., Kyoto (JP)

( * ) Notice: Subject to any disclaimer, the term of this patent is extended or adjusted under 35 U.S.C. 154(b) by 0 days.

(21) Appl. No.: 15/514,761

(22) PCT Filed: Mar. 13, 2015

(86) PCT No.: PCT/JP2015/057484
§ 371 (c)(1),
(2) Date: Mar. 27, 2017

(87) PCT Pub. No.: WO2016/051819
PCT Pub. Date: Apr. 7, 2016

(65) Prior Publication Data
US 2017/0217656 A1    Aug. 3, 2017

(30) Foreign Application Priority Data

Sep. 30, 2014  (JP) ................................. 2014-200410

(51) Int. Cl.
*A61B 17/06*  (2006.01)
*B65D 75/30*  (2006.01)
(Continued)

(52) U.S. Cl.
CPC ..... *B65D 75/5855* (2013.01); *A61M 37/0015* (2013.01); *B26F 1/40* (2013.01);
(Continued)

(58) Field of Classification Search
CPC ............... B65D 75/30; B65D 75/5855; A61M 37/0015; A61M 2037/0053;
(Continued)

(56) References Cited

U.S. PATENT DOCUMENTS 5,423,737 A * 6/1995 Cartmell ............... A61F 13/023
206/440
5,505,306 A * 4/1996 Akemi ................. A61F 15/001
206/438
(Continued)

FOREIGN PATENT DOCUMENTS

JP  2010-094414 A  4/2010
JP  2012-055343 A  3/2012
(Continued)

OTHER PUBLICATIONS

International Search Report in PCT/JP2015/057484 dated Jun. 16, 2015.

*Primary Examiner* — Luan K Bui
(74) *Attorney, Agent, or Firm* — Global IP Counselors, LLP

(57) ABSTRACT

A microneedle-sheet packaging body includes a microneedle sheet, a forming sheet, and a support body. The microneedle sheet includes a substrate, and a plurality of microneedles formed on a lower surface of the substrate. The forming sheet is tightly adhered to the lower surface of the substrate. The forming sheet includes a plurality of micro-recess parts in which the plurality of microneedles are housed. The support body is fixed to an upper surface of the substrate of the microneedle sheet and is further fixed to the forming sheet around the substrate. Thus, the microneedle-sheet packaging body protects a plurality of microneedles on the microneedle sheet.

9 Claims, 13 Drawing Sheets

(51) Int. Cl.
  *B65D 75/58* (2006.01)
  *A61M 37/00* (2006.01)
  *B26F 1/40* (2006.01)

(52) U.S. Cl.
  CPC ..... *B65D 75/30* (2013.01); *A61M 2037/0023* (2013.01); *A61M 2037/0053* (2013.01); *A61M 2209/06* (2013.01)

(58) Field of Classification Search
  CPC ....... A61M 2209/06; A61M 2037/0023; B26F 1/40; A61F 15/001
  USPC ............... 206/438, 440, 441; 156/245, 278; 424/449; 604/46, 272, 506
  See application file for complete search history.

(56) References Cited

U.S. PATENT DOCUMENTS

| | | | |
|---|---|---|---|
| 7,396,975 B2 * | 7/2008 | Sigurjonsson | A61F 13/0203 206/440 |
| 2010/0168715 A1 | 7/2010 | Cassemeyer et al. | |
| 2010/0256568 A1 * | 10/2010 | Frederickson | A61M 37/0015 604/173 |
| 2010/0305516 A1 * | 12/2010 | Xu | A61M 37/0015 604/272 |
| 2012/0101457 A1 | 4/2012 | Kato | |
| 2014/0158572 A1 * | 6/2014 | Jensen | A61F 15/002 206/441 |
| 2014/0339117 A1 * | 11/2014 | Quan | A61M 37/0015 206/438 |
| 2015/0335870 A1 * | 11/2015 | Quan | A61F 13/0008 604/46 |
| 2016/0082240 A1 * | 3/2016 | Ueno | A61K 9/0021 604/46 |
| 2017/0128708 A1 * | 5/2017 | Ueno | A61M 37/0015 |

FOREIGN PATENT DOCUMENTS

| | | |
|---|---|---|
| JP | 2014-113318 A | 6/2014 |
| WO | 2011002034 A1 | 1/2011 |

* cited by examiner

MICRONEEDLE-SHEET PACKAGING BODY AND METHOD OF MANUFACTURING THE SAME

CROSS-REFERENCE TO RELATED APPLICATION

This U.S. National stage application claims priority under 35 U.S.C. § 119(a) to Japanese Patent Application No. 2014-200410, filed in Japan on Sep. 30, 2014, the entire contents of Japanese Patent Application No. 2014-200410 are hereby incorporated herein by reference.

BACKGROUND

Field of the Invention

The present invention relates to a microneedle-sheet packaging body including a plurality of microneedles, and to a method of manufacturing the same.

Background Art

A resin sheet having a plurality of minute recessed parts is utilized as, for example, a microneedle-forming die for manufacturing a plurality of microneedles on a microneedle sheet (e.g., refer to PCT International Publication No. WO2011/002034). Furthermore, one example of a microneedle sheet is a transdermal patch. A transdermal patch is used as one means of noninvasively administering a drug or the like via the body surface of an organism, such as the skin or a mucous membrane. In such a case, the drug is adhered to the microneedles.

SUMMARY

Each microneedle of the plurality of microneedles of the microneedle sheet has a minute shape that is damaged relatively easily. Furthermore, after a completed microneedle sheet is packaged and ready to be shipped and transported, it is necessary to take measures to ensure that the microneedles do not get damaged. However, an effective measure to protect the microneedles inside the packaging has yet to be proposed.

An object of the present invention is to protect a plurality of microneedles of a microneedle sheet.

Aspects of the present invention are explained below as the technical solution. These aspects can be arbitrarily combined as needed.

According to one aspect of the present invention, a microneedle-sheet packaging body includes a microneedle sheet, a sheet member, and a sheet-shaped base material.

The microneedle sheet includes a sheet-shaped main body and a plurality of microneedles formed on a first surface of the main body.

The sheet member is tightly adhered to the first surface of the main body. The sheet member includes a plurality of micro-recess parts in which the plurality of microneedles are housed.

The sheet-shaped base material is fixed to a second surface of the main body of the microneedle sheet and is further fixed to the sheet member around the main body.

In this packaging body, the microneedle sheet is formed in the sheet member, and the state at the time when the microneedle sheet was formed is maintained. Specifically, the plurality of microneedles of the microneedle sheet are formed by the plurality of micro-recess parts of the sheet member and is also subsequently protected by the plurality of micro-recess parts. That is, the plurality of microneedles of the microneedle sheet are reliably protected.

In addition, the packaging body includes the sheet-shaped base material, which is fixed to the second surface of the main body of the microneedle sheet and is further fixed to the sheet member around the main body, and therefore the microneedle sheet is reliably protected.

The packaging body may further includes an adhesive. The adhesive is fixed to a surface of the sheet-shaped base material on the sheet member side. The adhesive is adhered to the second surface of the main body of the microneedle sheet, and is further adhered to the sheet member around the main body.

In the packaging body, the sheet-shaped base material is fixed to the microneedle sheet and the sheet member by the adhesive layer. Accordingly, the sheet-shaped base material tends not to peel off of the microneedle sheet and the sheet member. In addition, when the sheet-shaped base material is peeled off of sheet member, together with the microneedle sheet, and then the microneedle sheet can be stuck to the target by using the sheet-shaped base material and the adhesive.

The peel strength between the sheet-shaped base material and the microneedle sheet may be higher than the peel strength between the microneedle sheet and the sheet member.

In the packaging body, when the support body is peeled from the forming sheet, the microneedle sheet is reliably peeled from the sheet member.

The microneedle sheet may include a projecting part. The projecting part extends from the main body in a sheet-surface direction and is interposed between the sheet-shaped base material and the sheet member.

In this packaging body, the support body does not contact the forming sheet at the location of the projecting part of the microneedle sheet, and therefore the bonding strength between the forming sheet and other members is low at that portion of the outer-perimeter part. Accordingly, the sheet-shaped base material and the microneedle sheet can be easily peeled from the sheet member by holding and pulling, by hand, an edge of the projecting part of the microneedle sheet.

According to another aspect of the present invention, a microneedle sheet packaging body manufacturing method includes:

forming a plurality of micro-recess parts on a whole-sheet member;

supplying a microneedle material to the whole-sheet member such that a whole-microneedle sheet is formed. The whole-microneedle sheet includes a main body and a plurality of microneedles. The microneedles are formed on a first surface of the main body and are disposed inside the plurality of micro-recess parts;

punching the whole-microneedle sheet such that a desired plurality of individual microneedle sheets are formed, and subsequently eliminating an unnecessary part;

fixing a whole-sheet-shaped base material to the plurality of individual microneedle sheets; and punching, in units of the plurality of individual microneedle sheets, the whole-sheet member and the whole-sheet-shaped base material such that a plurality of the microneedle-sheet packaging bodies are formed, each microneedle-sheet packaging body having the individual microneedle sheet, an individual sheet member, and an individual sheet-shaped base material.

In the packaging body manufactured by the present manufacturing method, the microneedle sheet is formed in the sheet member, and the state at the time when the microneedle sheet was formed is maintained. Specifically, the plurality of microneedles of the microneedle sheet are formed by the plurality of micro-recess parts of the sheet member and are also subsequently protected by the plurality of micro-recess parts. That is, the plurality of microneedles of the microneedle sheet are reliably protected.

In addition, because the packaging body includes the individual sheet-shaped base material, which corresponds to individual microneedle sheet and is fixed to the sheet member, each individual microneedle sheet is protected.

Furthermore, in the present manufacturing method, the plurality of microneedle sheet packaging bodies are formed all at once by the step of punching out the whole sheet member and the sheet-shaped base material in the units of the individual microneedle sheet. Accordingly, mass production with a small number of processes becomes possible.

In the step of fixing the whole-sheet-shaped base material, the whole-sheet-shaped base material may be fixed to the whole-sheet member around the individual microneedle sheets.

In the present manufacturing method, the whole support body is fixed to the whole forming sheet at the periphery of each microneedle sheet, and therefore the last article-punching step can create the state wherein the individual sealing sheets are fixed to the individual forming sheets at the peripheries of the individual microneedle sheets. Thereby, the individual microneedle sheets are protected from outside contamination.

Furthermore, it is possible to roughly handle the materials in a series of the steps, which contributes the improvement on the productivity of the microneedle sheets.

According to a microneedle-sheet packaging body and a microneedle-sheet packaging body manufacturing method of the present invention, the plurality of microneedles of the microneedle sheet are reliably protected.

DESCRIPTION OF EMBODIMENTS

1. First Embodiment (1) Microneedle-Sheet Packaging Body

Figure 1:
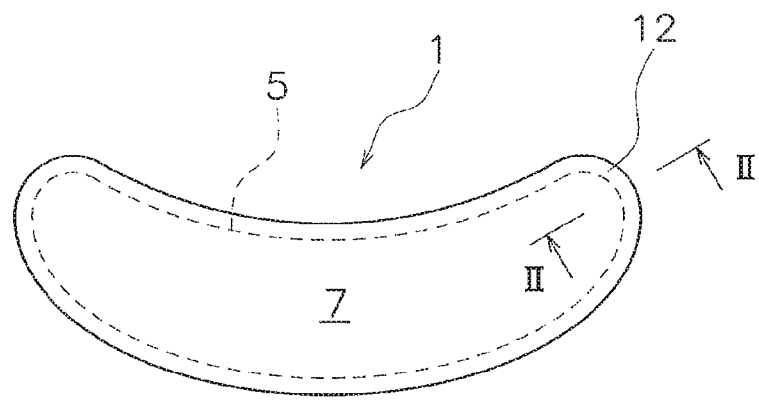
FIG. 1 is a plan view of the microneedle-sheet packaging body according to a first embodiment of the present invention.
Figure 2:
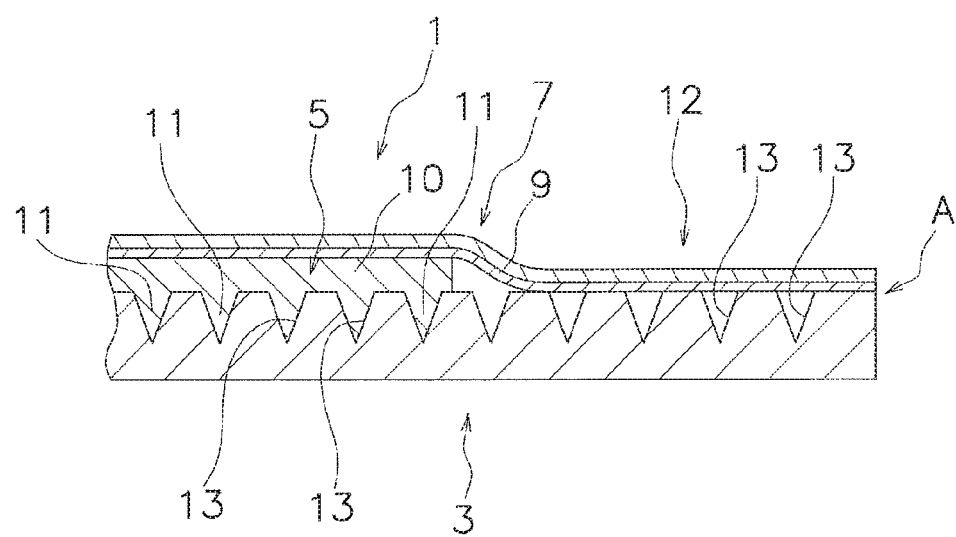
FIG. 2 is a cross-sectional view taken along line II-II in FIG. 1 and is a cross-sectional view of the microneedle-sheet packaging body.

A microneedle-sheet packaging body 1 according to the present embodiment will be explained, with reference to FIG. 1 and FIG. 2. FIG. 1 is a plan view of the microneedle-sheet packaging body according to the first embodiment of the present invention. FIG. 2 is a cross-sectional view taken along line II-II in FIG. 1 and is a cross-sectional view of the microneedle-sheet packaging body.

The microneedle-sheet packaging body 1 includes a microneedle sheet 5, a microneedle-forming sheet 3 (one example of a sheet member; hereinbelow, called a forming sheet 3), and a support body 7 (one example of a sheet-shaped base material). The forming sheet 3 and the support body 7 are primary packaging materials that package the microneedle sheet 5. Thus, the packaging body 1 is a primary package, the shape of which is a flat, plate-shaped piece. Accordingly, the degrees of freedom of a subsequent secondary package are increased. For example, a vacuum package or a design package is possible.

Furthermore, in the embodiment below, the microneedle sheet housed in the primary packaging material is singular, but a plurality of the microneedle sheets may be housed.

(1-1) Microneedle Sheet

The microneedle sheet 5 is a member that is packaged by the primary packaging material, which was discussed above, and is used by being removed from the primary packaging material as needed. The microneedle sheet 5 is a sheet-shaped article whereon a plurality of microneedles 11 are formed on one surface. The thickness of the microneedle sheet 5 is approximately several hundred micrometers. The overall planar shape of the microneedle sheet 5 is smoothly curved and has a crescent-moon shape, as shown in FIG. 1. The shape of the microneedle sheet 5 may be a circle, an ellipse, a triangle, a quadrangle, a square, a magatama (comma), or some other shape. If the microneedle sheet 5 is, for example, a quadrangle, then one side is approximately several to several tens of millimeters.

The structure of the microneedle sheet 5 will now be further explained, with reference to FIG. 1. The microneedle sheet 5 includes a sheet-shaped substrate 10 (one example of a sheet-shaped main body) and the plurality of microneedles 11 (one example of microneedles). The plurality of microneedles 11 are formed on a lower surface (one example of a first surface) of the substrate 10. Each microneedle 11 has, for example, a conical shape or a pyramidal shape with a height of 10-1,000 µm, wherein the ratio of the cross-sectional diameter, at the base, to the height (cross-sectional-diameter:height) is 1:0.2-1:5 and the aspect ratio (height/cross-sectional diameter) is high.

The microneedle sheet 5 is a transdermal patch that is used, for example, to administer a drug or the like by being affixed such that it contacts the skin of a person. Specifically, the administration of the drug or the like is promoted by the substrate 10 being stuck onto the skin and the microneedles 11 piercing the skin.

The microneedle sheet 5 includes, as the principal materials, for example, a water soluble drug and a water-soluble macromolecule, such as hyaluronate, a water-soluble collagen, dextran, chondroitin sulfate, or the like, to which the drug has been added. Furthermore, the water-soluble macromolecule to which a pharmaceutical agent has been added is preferably an in-vivo-soluble, water-soluble macromolecule, for example, an in-vivo-soluble, water-soluble macromolecule such as sodium chondroitin sulfate, hyaluronate, or dextran.

Furthermore, the water-soluble macromolecule is a substance of at least 1 selected from the group consisting of sodium chondroitin sulfate, hyaluronate, a collagen (or a hydrolyzed collagen), gelatin, a glycogen, dextran, dextrin, dextran sulfate, cyclodextrin, chitosan, proteoglycan, pullulan, hydroxypropylcellulose, alginic acid, agarose, glycogen, carboxymethyl cellulose, hydroxyethyl cellulose, hydroxypropylcellulose, polyvinylpyrrolidone, polyvinyl alcohol, and a carboxyvinyl polymer. One of these water-soluble macromolecules may be used alone, or a plurality thereof may be used in combination.

(1-2) Support Body

The support body 7 is a sheet for supporting the microneedle sheet 5 and is a material having good air permeability, such as, for example, a nonwoven fabric. The support body 7 is fixed to an upper surface (one example of a second surface) of the substrate 10 of the microneedle sheet 5 and is adhered farther therearound to an upper surface of the forming sheet 3.

More specifically, an adhesive layer 9 (one example of an adhesive) is provided entirely across the lower surface (one example of a sheet-member-side surface) of the support body 7. The support body 7 is fixed to the upper surface of the microneedle sheet 5 by the adhesive layer 9. Specifically, the adhesive layer 9 is adhered to the upper surface of the substrate 10 of the microneedle sheet 5 and, furthermore, is adhered to the forming sheet 3 at an outer-perimeter part 12 around the substrate 10. Thus, the adhesive layer 9 is provided on a lower surface of the support body 7 also at an outer-perimeter part 12, which is further on the outer-perimeter side of the microneedle sheet 5. Accordingly, the support body 7 tends not to peel off of the microneedle sheet 5 and the forming sheet 3. In addition, after the support body 7 has been peeled, together with the microneedle sheet 5, off of the forming sheet 3, the adhesive layer 9 on the outer-perimeter side is used in sticking the support body 7 and the microneedle sheet 5 to the target.

Furthermore, in FIG. 2, micro-recess parts 13 are formed, on the upper surface of the forming sheet 3, at a portion (corresponding to the outer-perimeter part 12) of the outer-perimeter part of the support body 7 at which the adhesive layer 9 is fixed. Thereby, the surface to which the adhesive layer 9 adheres becomes smaller; thereby, the adhesive strength of the adhesive layer 9 is maintained. However, the micro-recess parts 13 do not have to be formed at the abovementioned portion.

Furthermore, the adhesive layer 9 is composed of, for example, a rubber-based material, an acrylic-based material, a silicone-based material, or a urethane-based material.

(1-3) Forming Sheet

The forming sheet 3 is a member for both forming the microneedles 11 and protecting the microneedles 11 after forming. The forming sheet 3 is stuck to the lower surface of the microneedle sheet 5. In addition, as shown in FIG. 2, the plurality of micro-recess parts 13, which is for forming and housing the microneedles 11 of the microneedle sheet 5, is formed on the upper surface of the forming sheet 3. Furthermore, each micro-recess part 13 is an indentation that is open toward the upper side and does not pass through the microneedle sheet 5.

Taking into consideration that the forming sheet 3 is used as the member that forms the plurality of micro-recess parts 13, the forming sheet 3 is composed of, for example, a polyolefin based resin such as polyethylene, polypropylene, and the like. That is, the forming sheet 3 is preferably a hydrophobic sheet wherein the adhesive agent is re-peelable.

When the support body 7 is to be peeled from the forming sheet 3, the following approaches may become necessary to ensure that the microneedle sheet 5 reliably follows from the forming sheet 3. Firstly, an adhesive layer with a sufficiently high adhesive strength is selected as the adhesive layer 9. Secondly, the adhesive strength between the forming sheet 3 and the microneedle sheet 5 is increased by subjecting the surface of the forming sheet 3 to a hydrophilic treatment in advance; however, both the forming sheet 3 and the microneedle sheet 5 may be made easy to peel by decreasing the extent of that treatment. Furthermore, the first idea and the second idea may be combined.

Furthermore, the bonding strength of both may be increased by aging, in which time is taken to cause the adhesive layer 9 and the microneedle sheet 5 to set.

The forming-and-protecting-structure of the microneedle sheet is configured by the microneedle sheet 5 and the forming sheet 3, which are tightly adhered to one another as discussed above.

(1-4) Packaging Material

Next, a secondary packaging body 19, which houses the packaging body 1 that serves as a primary packaging body, will be explained, with reference to FIG. 3. The secondary packaging body 19 includes a packaging member 21 and a sealing sheet 23; the packaging body 1 is packaged by the two sheets being stuck together.

The packaging member 21 is a sheet-shaped member and is composed of a common resin material. As shown in FIG. 3, the packaging member 21 includes a housing part 21*a* for housing the packaging body 1. The housing part 21*a* is a recessed part that is formed on an inner side of the packaging member 21.

The sealing sheet 23 is a sheet-shaped member that is stuck to the inner-side surface of the packaging member 21 in order to seal the packaging body 1 inside the housing part 21*a* between the sealing sheet 23 and the packaging member 21. Specifically, the sealing sheet 23 includes, for example, as a general structure, a surface-resin layer (not shown) and a metal layer (not shown). The surface-resin layer is capable of being printed upon and further functions to protect the metal layer. The metal layer is provided on a lower surface of the surface-resin layer. The metal layer is composed of aluminum or an alloy thereof and has a high degree of moisture proofness.

A bonding layer (not shown) is provided on a surface on the side of the metal layer opposite the surface-resin layer. The bonding layer is for bonding the sealing sheet 23 to the packaging member 21.

Thus, the sealing sheet 23 is stuck to the inner-side surface of the packaging member 21 in the state wherein the sealing sheet 23 covers the packaging body 1, and thereby both seal the housing part 21*a*.

Figure 3:
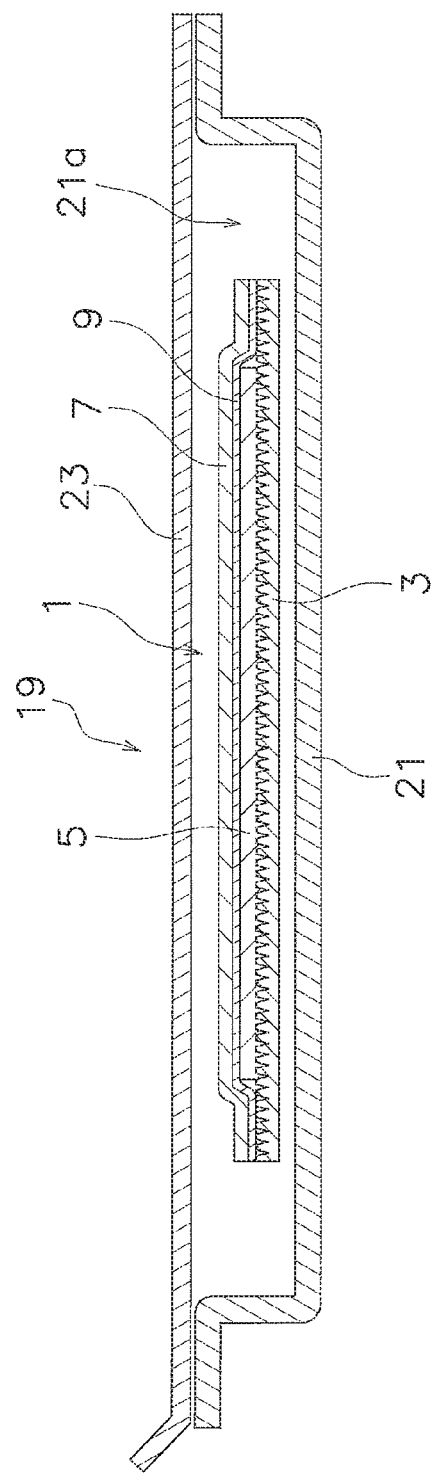
FIG. 3 is a schematic cross-sectional view of a secondary packaging body of a microneedle sheet.

As shown in FIG. 3, the packaging body 1 is movably disposed inside the packaging member 21 and the sealing sheet 23. However, the packaging body 1 may be fixed to the packaging member 21 by some means.

In the present embodiment, the packaging body 1 is not positioned inside the secondary packaging body 19; however, the packaging body 1 has a structure that protects the microneedle sheet 5, and therefore the plurality of microneedles 11 of the microneedle sheet 5 are reliably protected.

(1-5) Method of Use

Figure 6:
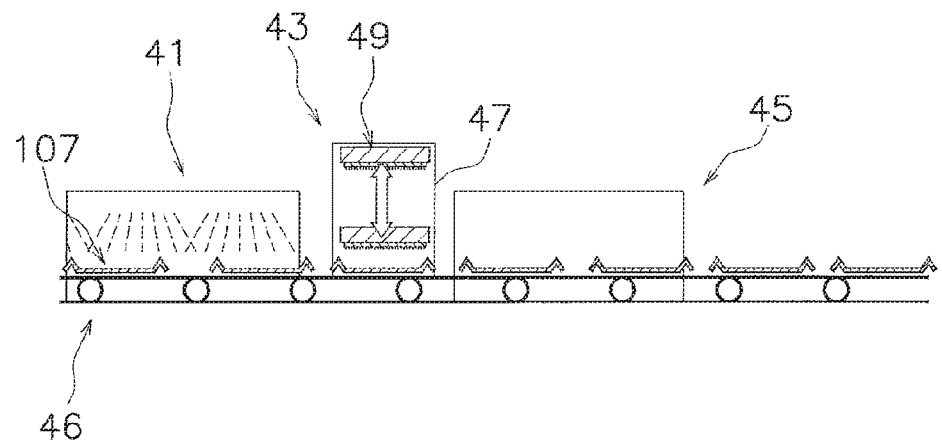
FIG. 6 is a schematic drawing that illustrates a preheating and forming process.

When the packaging body 1 is to be removed from the secondary packaging body 19, the user peels the sealing sheet 23 from the packaging member 21, as shown in FIG. 6, and subsequently the packaging body 1 is removed from the housing part 21*a*. Thereby, the microneedle sheet 5, in which the plurality of microneedles 11 are protected by the forming sheet 3, can be obtained.

Next, the user peels the microneedle sheet 5 from the forming sheet 3. Specifically, the user peels the support body 7 from the forming sheet 3 by grasping the outer-perimeter part (refer to arrow A in FIG. 2) of the support body 7. At this time, the microneedle sheet 5 separates from the forming sheet 3, that is, the microneedles 11 separate from the micro-recess parts 13.

As a result, the user becomes able to use the support-body-attached microneedle sheet, which includes the support body 7 and the microneedle sheet 5, in accordance with the intended purpose. In the case of a transdermal patch, the support-body-attached microneedle sheet is stuck to the skin of a person. In this case, the outer-perimeter part of the support body 7 sticks to the skin via the adhesive layer 9, and the microneedles 11 of the microneedle sheet 5 contact the skin. That is, the first adhesive layer 9 functions as an adhesive portion after the support-body-attached microneedle sheet has been removed.

As discussed above, the object is achieved by just peeling off and then sticking the support-body-attached microneedle sheet, and therefore usage is simple.

The peel strength between the support body 7 and the microneedle sheet 5 is preferably higher than the peel strength between the microneedle sheet 5 and the forming sheet 3. The reason for that is to make it so that, when the support body 7 is peeled from the forming sheet 3, the microneedle sheet 5 is reliably peeled from the forming sheet 3. The peel strength between the support body 7 and the microneedle sheet 5 is, for example, 4-5 N/20 mm. The peel strength between the microneedle sheet 5 and the forming sheet 3 is, for example, 1-2 N/20 mm.

(2) Method of Manufacturing the Microneedle Sheet Packaging Body

A method of manufacturing the microneedle sheet packaging body 1 will now be explained, with reference to FIG. 4 to FIG. 23. The plurality of manufacturing processes are explained below.

(2-1) Manufacture of Microneedle-Sheet, Forming-and-Protecting-Structure Preform Hereinbelow, a step of forming a plurality of micro-recess parts 13 on the blank 107 (the whole-forming sheet 3A).

Figure 4:
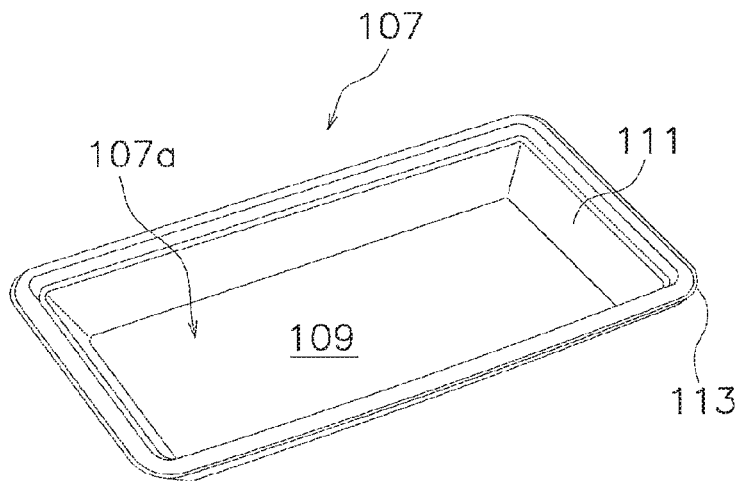
FIG. 4 is an oblique view of a blank of a microneedle-forming sheet.
Figure 5:
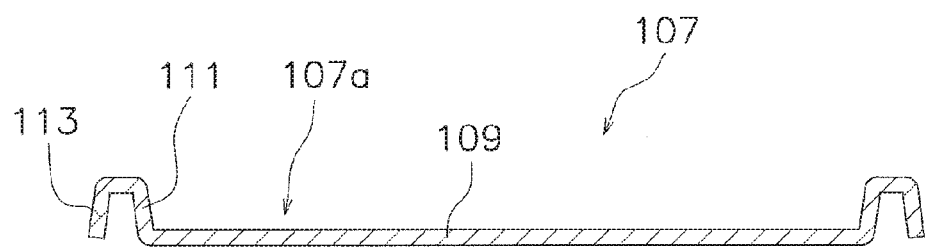
FIG. 5 is a cross-sectional view of the blank of the microneedle-forming sheet.

First, as shown in FIG. 4 and FIG. 5, a blank 107, which will constitute the forming sheet 3, is prepared. FIG. 4 is an oblique view of a blank of the microneedles forming sheet. FIG. 5 is a cross-sectional view of a blank of the microneedles forming sheet. As is clear from the figures, the blank 107 includes a bottom-surface part 109 and side-surface parts 111. The bottom-surface part 109 is, for example, a quadrangular, flat, plate-shaped portion. The side-surface parts 111 are plate-shaped portions that extend upward from four sides of the bottom-surface part 109 and form a recessed part 107*a*. Furthermore, a folded part 113 is formed over the entire perimeter at upper ends of the side-surface parts 111. In a cross section, the folded part 113 extends toward the outer-perimeter side from the recessed part 107*a* and further extends downward.

Figure 8:
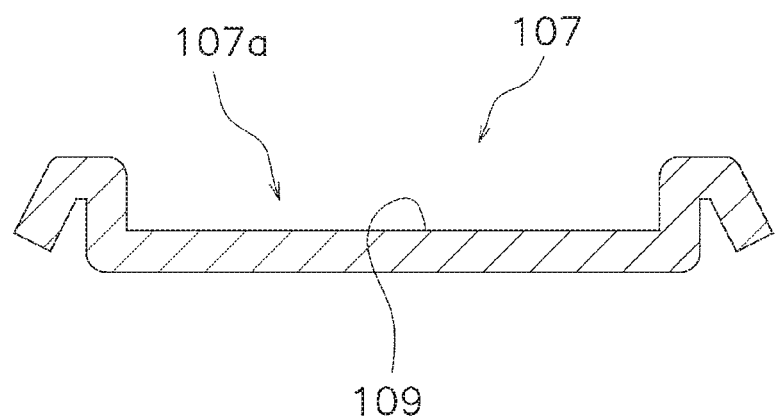
FIG. 8 is a schematic cross-sectional view that shows the state before formation of the blank.

A process of preheating and forming the blank 107 will now be explained, with reference to FIG. 8 to FIG. 9. FIG. 8 is a schematic drawing that illustrates the preheating and forming process. As shown in the figure, a heating chamber 41, a forming apparatus 43, and a cooling chamber 45 are provided in series.

In the heating chamber 41, the blank 107 is preheated prior to being formed. The forming apparatus 43 forms the micro-recess parts 13 on the blank 107. In the cooling chamber 45, the blank 107 is cooled. The blank 107 is transported between the apparatuses by a conveyor 46.

Figure 7:
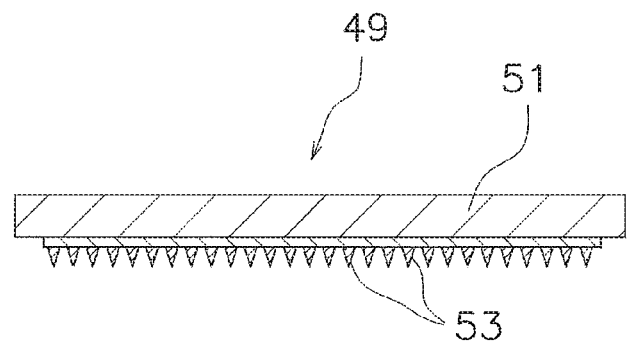
FIG. 7 is a cross-sectional view of a press die.

The forming apparatus 43 is an apparatus for forming the plurality of minute micro-recess parts 13 on the bottom-surface part 109 of the blank 107. As shown in the figure, the forming apparatus 43 includes a high-precision press 47 and a pincushion-shaped press die 49 (a micro-spike die). As shown in FIG. 7, the press die 49 includes a press part 51. FIG. 7 is a cross-sectional view of the press die. The press part 51 has a shape that matches the bottom-surface part 109 of the blank 107, and, on its lower surface, the press part 51 includes a plurality of fabricating projections 53.

As shown in FIG. 8, prior to the forming work, the bottom-surface part 109 of the blank 107 is flat. FIG. 8 is a schematic cross-sectional view that shows the state prior to the forming of the blank.

Owing to the preheating prior to the forming, the blank 107 has already been softened when the press die 49 contacts the bottom-surface part 109. As a result, as shown in FIG. 9, the fabricating projections 53 form the plurality of micro-recess parts 13 on the bottom-surface part 109. Furthermore, the control of the press is formed by a machine capable of controlling the pressing location, the pressing pressure, the pressing time, and the like with high precision. Although it needs working time, heating and cooling the press die 49 may achieves the previous series of the steps.

Figure 9:
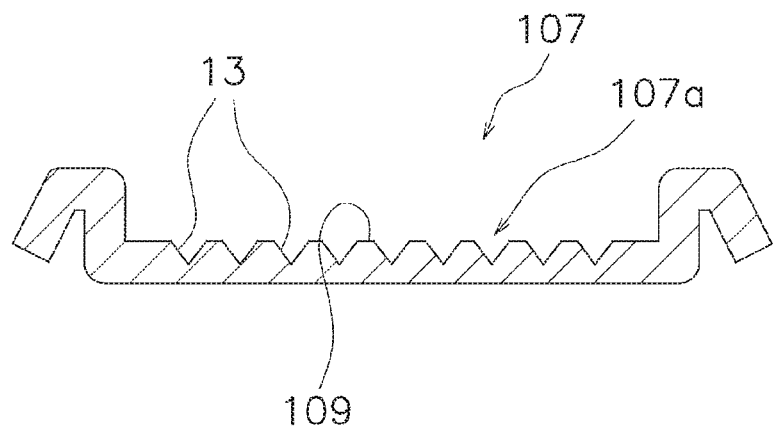
FIG. 9 is a schematic cross-sectional view that shows the state after the formation of the blanket.

FIG. 9 is a schematic cross-sectional view that shows the state after the forming of the blank. As shown in the figure, each micro-recess part 13 has, for example, a conical shape or a pyramidal shape and is open toward the upper side in the figure.

Hereinbelow, a step of supplying the microneedles material 56 to the blank 107 (i.e., the whole-forming sheet 3A) such that whole microneedle sheet 5A, which includes the substrate 10 and a plurality of microneedles 11 formed on the lower surface of the substrate 10 and housed in the plurality of micro-recess parts 13.

Figure 10:
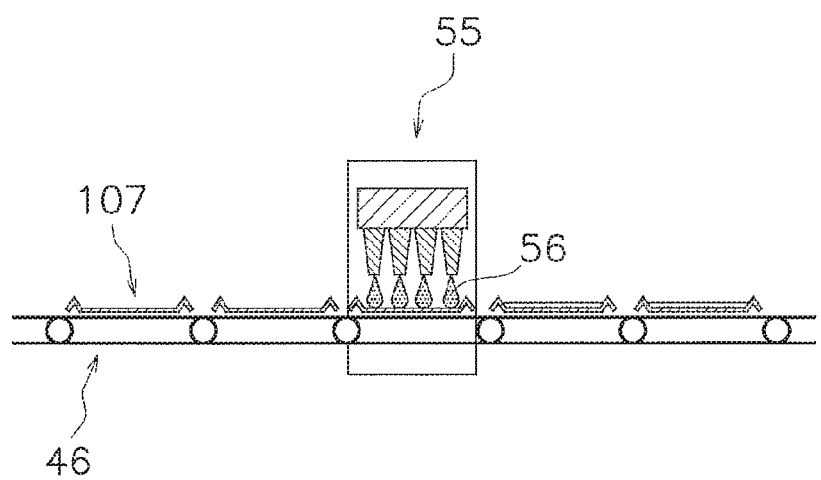
FIG. 10 is a schematic drawing for explaining a process wherein microneedle materials are dripped onto the microneedle-forming sheets.
Figure 11:
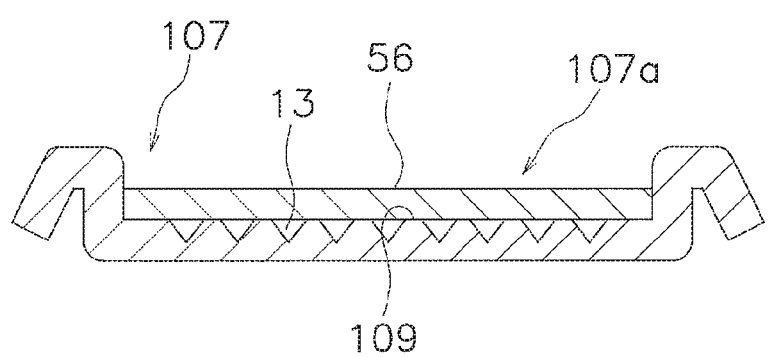
FIG. 11 is a schematic cross-sectional view of the microneedle-forming sheet filled with the microneedle material.

Next, the process in which a microneedles material 56 is supplied to the blanks 107 will be explained, with reference to FIG. 10 to FIG. 11. FIG. 10 is a schematic drawing for explaining a process of dripping a microneedles material onto the microneedles forming sheets. As shown in the figure, a dispenser 55 is provided. The dispenser 55 is an apparatus that drips the microneedles material 56 onto the recessed part 107a. The microneedles material 56 is, for example, sodium hyaluronate dissolved in a solvent consisting of water, etc. Furthermore, a medium wherein water-soluble macromolecules in addition to water are soluble is selected as the solvent. Thus, by supplying the microneedles material to each bottom-surface part 109, each bottom-surface part 109 is covered by the microneedles material 56, as shown in FIG. 11. FIG. 11 is a schematic cross-sectional view of the microneedles forming sheet filled with the microneedles material. Furthermore, in the present embodiment, the microneedles material 56 does not penetrate to the interior of the micro-recess parts 13, and consequently air remains in the micro-recess parts 13. In this case, an evacuation process (not shown) may be added.

Figure 12:
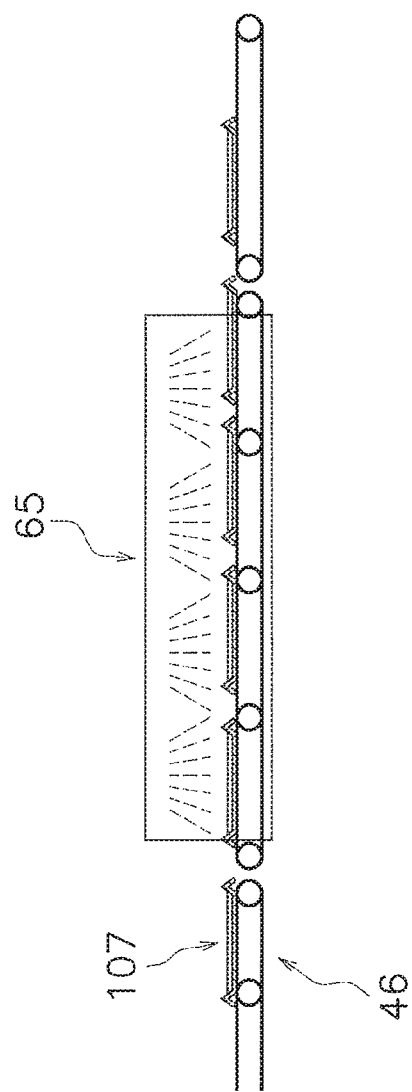
FIG. 12 is a schematic drawing for explaining a process of drying the microneedle materials.
Figure 13:
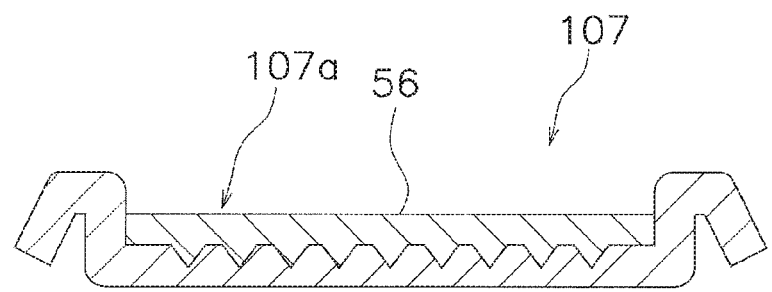
FIG. 13 is a schematic cross-sectional view of the microneedle-forming sheet filled with the microneedle material before the drying process.
Figure 14:
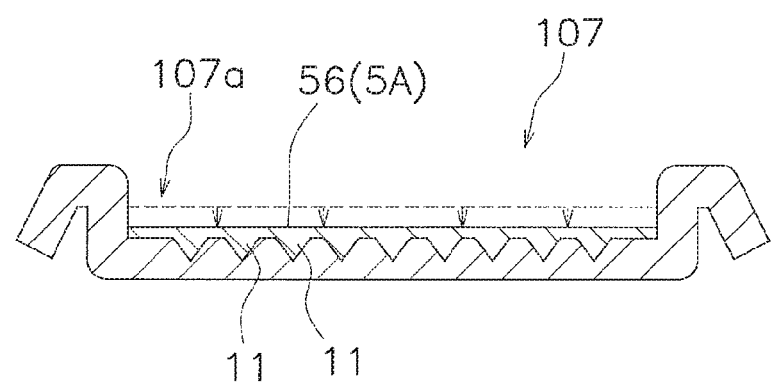
FIG. 14 is a schematic cross-sectional view of the microneedle-forming sheet filled with the microneedle material after the drying process.

Next, a process of drying and hardening the microneedles material 56 will be explained, with reference to FIG. 12 to FIG. 14. FIG. 12 is a schematic drawing for explaining a process of drying the microneedles material. As shown in the figure, a drying furnace 65 is provided. In the drying furnace 65, the microneedles material 56 for each of the blanks 107 is heated and thereby dried. Thereby, moisture and the solvent agent are evaporated from the microneedles materials 56. As a result, starting from the state shown in FIG. 13, the microneedles material 56 shrinks because of the drying, and the volume is reduced to the position shown in FIG. 14. In this state, the microneedles material 56 becomes the whole microneedle sheet 5A having the plurality of microneedles 11. FIG. 13 is a schematic cross-sectional view of the microneedles forming sheet filled with the microneedles material prior to the drying process. FIG. 14 is a schematic cross-sectional view of the microneedles forming sheet filled with the microneedles material after the drying process.

Figure 15:
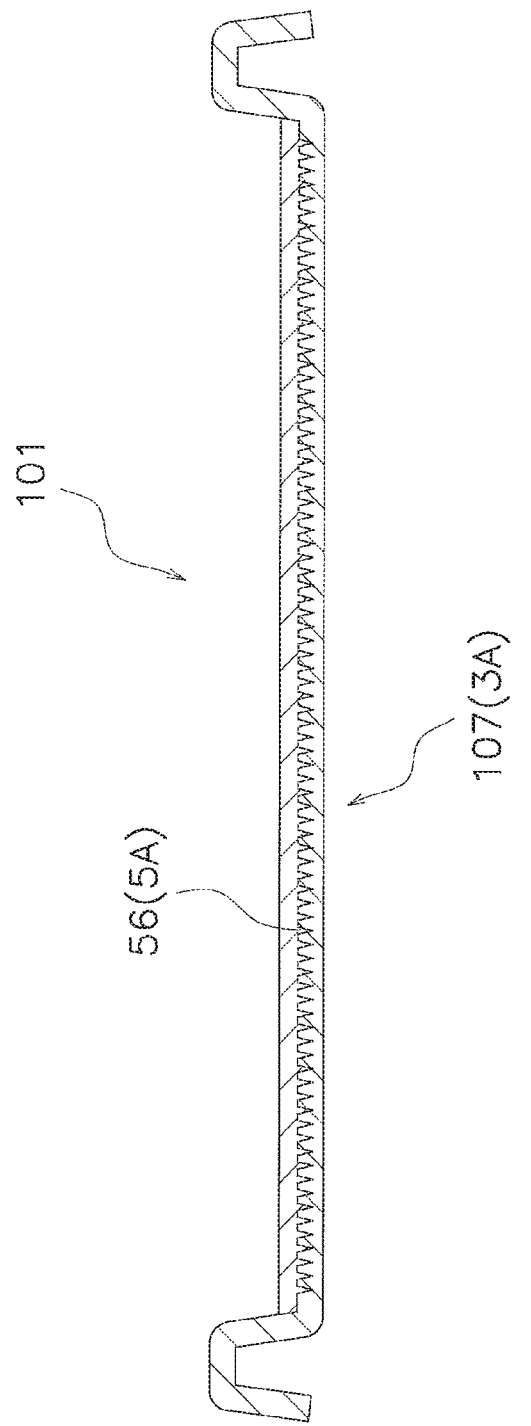
FIG. 15 is a cross-sectional view of a microneedle sheet, forming-and-protecting-structure preform.

As a result of the above, as shown in FIG. 15, a microneedle-sheet, forming-and-protecting-structure preform 101 (hereinbelow, called a preform 101) is obtained wherein is formed the microneedles material 56 (the whole microneedle sheet 5A) solidified on the bottom-surface part of the blank 107 (the whole forming sheet 3A). FIG. 15 is a cross-sectional view of the microneedle-sheet, forming-and-protecting-structure preform.

(2-2) Manufacture of the Packaging Body of Microneedle-Sheet

A method of manufacturing the packaging body 1 is explained below, with reference to FIG. 16 to FIG. 23.

Figure 18:
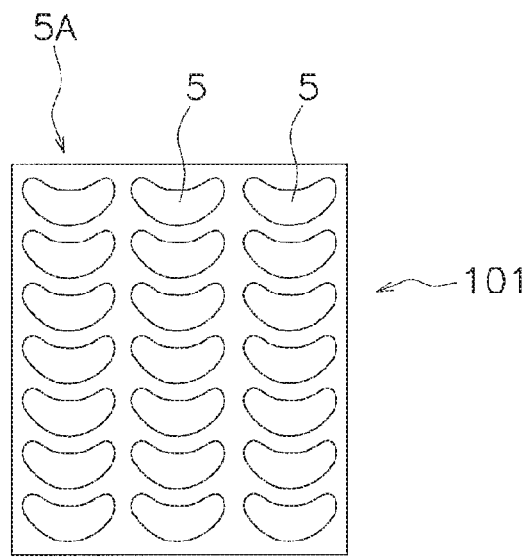
FIG. 18 is a plan view of the microneedle-sheet, forming-and-protecting-structure preform.
Figure 19:
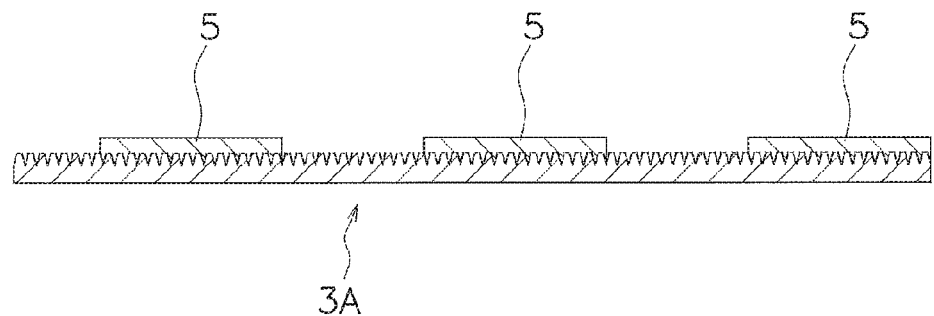
FIG. 19 is a schematic cross-sectional view for explaining a process of manufacturing the packaging body from the microneedle-sheet, forming-and-protecting-structure preform.
Figure 20:
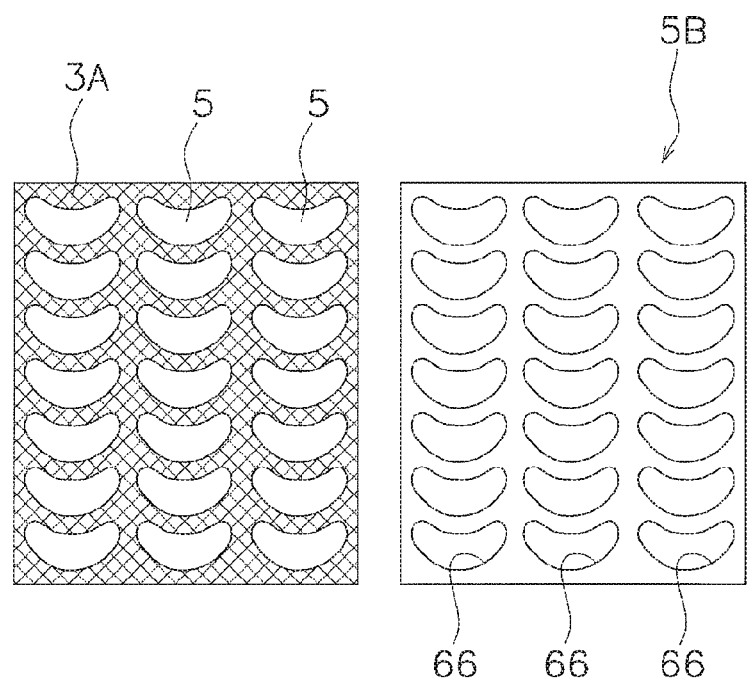
FIG. 20 is a plan view of the microneedle-sheet, forming-and-protecting-structure preform.

FIG. 16, FIG. 17, FIG. 19, FIG. 21, and FIG. 22 are schematic cross-sectional views for explaining a process of manufacturing the packaging body from the microneedle-sheet' forming-and-protecting-structure preform. FIG. 18, FIG. 20 and FIG. 23 are plan views of the microneedle-sheet's forming-and-protecting-structure preform.

First, the preform 101, wherein the whole microneedle sheet 5A has been formed on the bottom-surface part of the whole forming sheet 3A, is prepared.

A step of punching out the whole microneedle sheet 5A such that a desired plurality of the individual microneedle sheets 5 are formed and then eliminating unnecessary portions is explained below.

Figure 16:
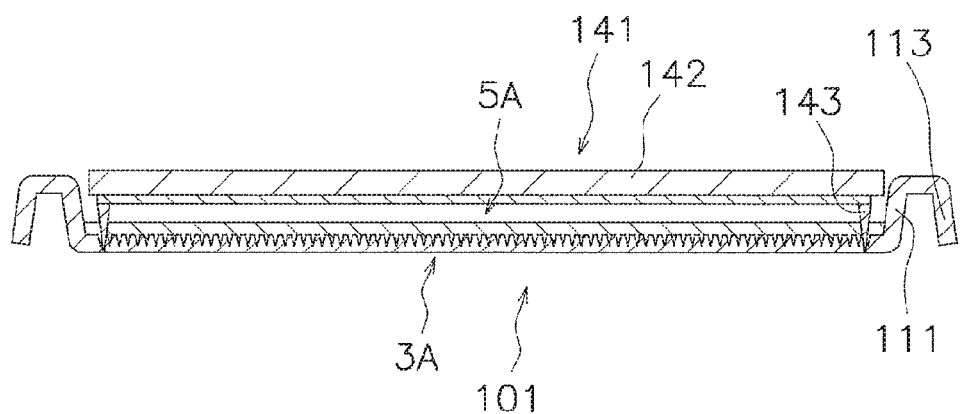
FIG. 16 is a schematic cross-sectional view for explaining a process of manufacturing the packaging body from the microneedle sheet, forming-and-protecting-structure preform.

As shown in FIG. 16, a cutting apparatus 141 is used. The cutting apparatus 141 has a press part 142 and a ring-shaped cutting blade 143. The cutting blade 143 is provided on a lower surface of the press part 142. The cutting blade 143 has a shape that corresponds to the outer perimeter of the bottom-surface part of the whole forming sheet 3A. As shown in FIG. 16, when the press part 142 is lowered and brought proximate to the preform 101, the cutting blade 143 cuts the preform 101 to its lower surface. As a result, the side-surface part 111 and the folded part 113 of the whole forming sheet 3A are cut off. As a result, the preform 101 becomes a planar sheet. Furthermore, a trimming die, such as an etching blade, an engraving blade, or a Thomson blade, can be used as the cutting blade.

Figure 17:
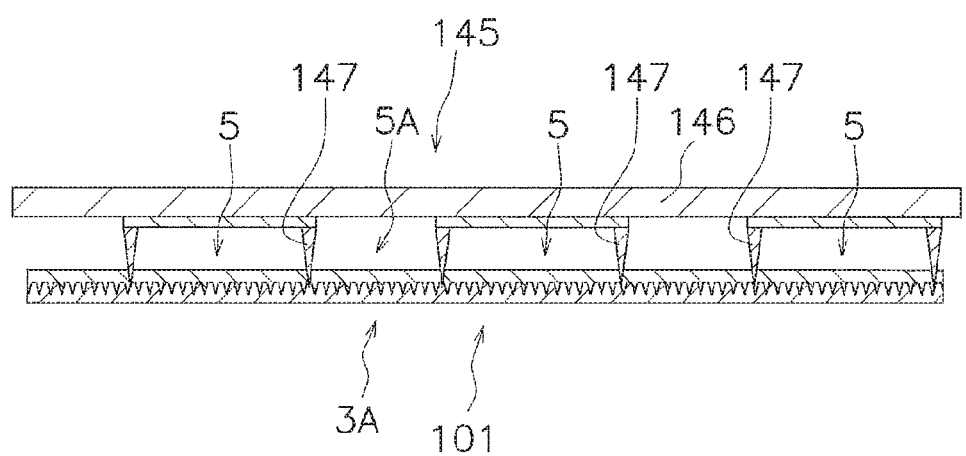
FIG. 17 is a schematic cross-sectional view for explaining a process of manufacturing the packaging body from the microneedle sheet, forming-and-protecting-structure preform.

Next, as shown in FIG. 17, a cutting apparatus 145 is used. The cutting apparatus 145 includes a press part 146 and a plurality of cutting blades 147. Each cutting blade 147 is provided on a lower surface of the press part 146. Each cutting blade 147 is ring shaped. As shown in FIG. 17, when the press part 146 is lowered and brought proximate to the preform 101, the cutting blades 147 cut portions of the solidified whole microneedle sheet 5A of the preform 101 to the lower surface, thereby forming the microneedle sheets 5. However, the cutting blades 147 do not reach the lower surface of the whole forming sheet 3A; that is, the cutting blades 147 do not cut the whole forming sheet 3A (performs a half-cut). As a result, as shown in FIG. 19, the plurality of microneedle sheets 5 punched out in shapes corresponding to the plurality of cutting blades 147 are obtained on the whole forming sheet 3A. FIG. 19 and the left view in FIG. 20 show a state after waste matter has been removed, and the right view in FIG. 20 shows a waste matter 5B. In the waste matter 5B, trim remnants 66, which are the remnants remaining after the plurality of microneedle sheets 5 have been eliminated, are formed.

Next, a step of fixing a whole support body 7A to the plurality of individual microneedle sheets 5 will be explained.

Figure 21:
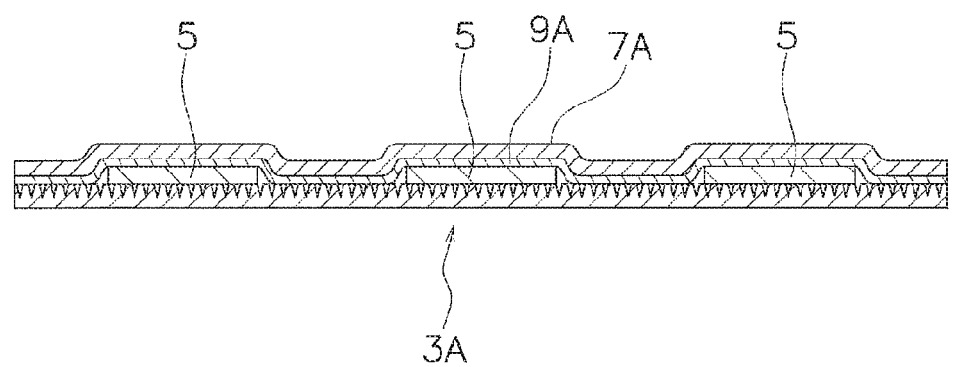
FIG. 21 is a schematic cross-sectional view for explaining a process of manufacturing the packaging body from the microneedle-sheet, forming-and-protecting-structure preform.

As shown in FIG. 21, the whole support body 7A, whose plane is a quadrangle corresponding to the whole forming sheet 3A, is fixed to each of the microneedle sheets 5. That is, the whole support body 7A is adhered across the entire surface of the whole forming sheet 3A. A whole adhesive layer 9A is provided entirely on a lower surface of the whole support body 7A.

At this time, the whole support body 7A is adhered not only to the microneedle sheets 5 but also to exposed parts of the upper surface of the whole forming sheet 3A. That is, in the step of fixing the whole support body 7A, the whole support body 7A is fixed to the whole forming sheet 3A at the periphery of each individual microneedle sheet 5.

Last, a step will be explained wherein, in units of the individual microneedle sheet 5, the whole forming sheet 3A and the whole support body 7A are punched out, thereby forming a plurality of the microneedle-sheet packaging bodies 1, each packaging body 1 including an individual microneedle sheet 5, an individual forming sheet 3, and an individual support body 7.

Figure 22:
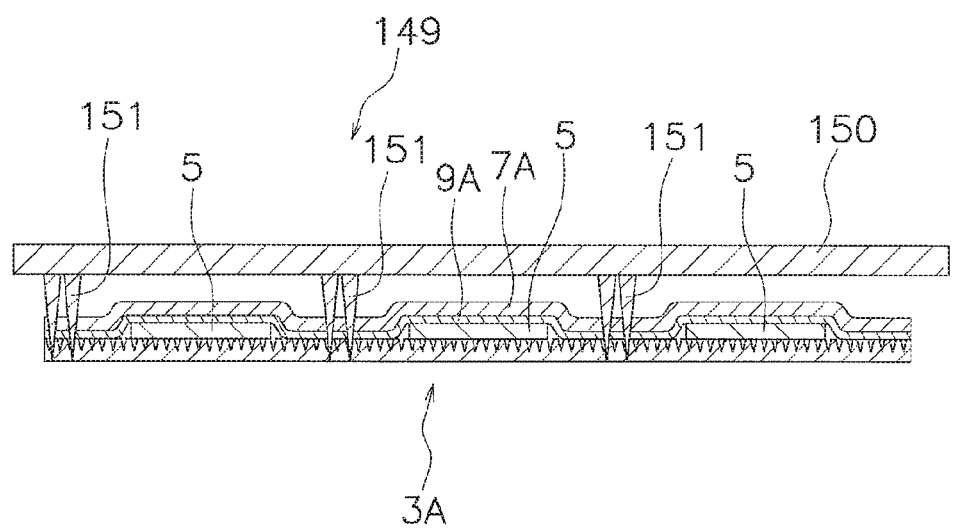
FIG. 22 is a schematic cross-sectional view for explaining a process of manufacturing the packaging body from the microneedle-sheet, forming-and-protecting-structure preform.
Figure 23:
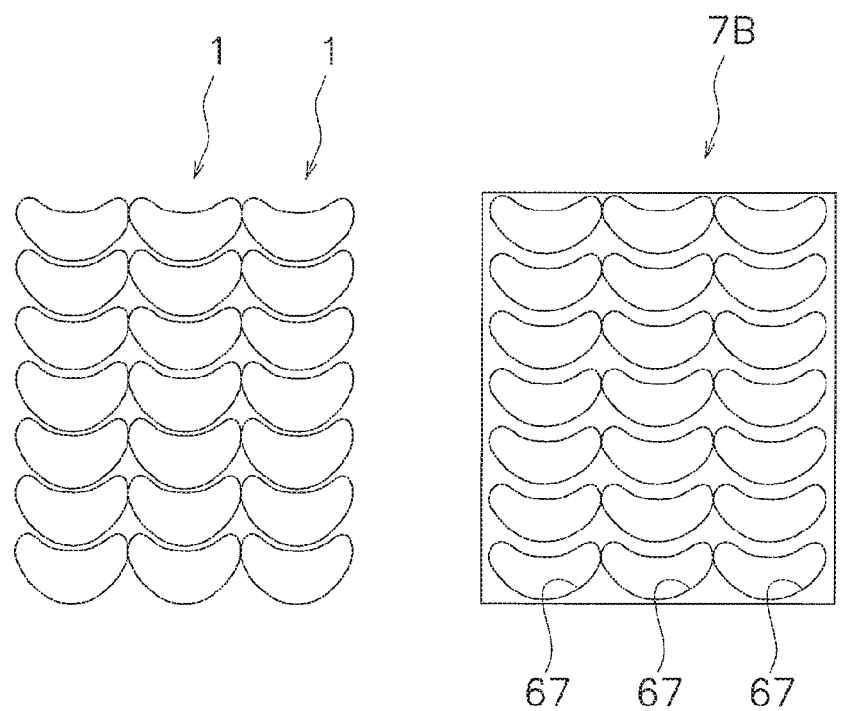
FIG. 23 is a plan view of the microneedle-sheet, forming-and-protecting-structure preform.

As shown in FIG. 22, a cutting apparatus 149 is used. The cutting apparatus 149 includes a press part 150 and a plurality of cutting blades 151. The cutting blades 151 are provided on a lower surface of the press part 150. Each cutting blade 151 is ring shaped and has a diameter larger than that of the cutting blade 147. When the press part 150 is lowered and brought proximate to the whole forming sheet 3A and the whole support body 7A, the cutting blades 151 cut, to the lower surface, the whole forming sheet 3A and the whole support body 7A at the outer perimeters of the individual microneedle sheets 5. As a result, as shown on the left side in FIG. 23, a plurality of the packaging bodies 1 are obtained. Furthermore, the drawing on the right side of FIG. 23 is waste matter 7B. In the waste matter 7B, trim remnants 67, which are the remnants remaining after the plurality of packaging bodies 1 have been cut out, are formed.

In the packaging body 1 manufactured by this manufacturing method, the microneedle sheets 5 are formed in the forming sheet 3 and, furthermore, their state at the time when they are formed is maintained. Specifically, the plurality of microneedles 11 of each microneedle sheet 5 are formed by the plurality of micro-recess parts 13 of the forming sheet 3; subsequently, too, the plurality of microneedles 11 are protected by the plurality of micro-recess parts 13. That is, the plurality of microneedles 11 of each microneedle sheet 5 are reliably protected.

In addition, because the packaging body 1 includes the support body 7, which corresponds to the microneedle sheet 5 and is fixed to the forming sheet 3, each individual microneedle sheet 5 is protected.

Furthermore, in the present manufacturing method, the plurality of microneedle sheet packaging bodies 1 are formed all at once by the last article-punching step (FIG. 22). Accordingly, mass production with a small number of processes becomes possible.

Furthermore, in the present manufacturing method, the whole support body 7A is fixed to the whole forming sheet 3A at the periphery of each microneedle sheet 5, and therefore the last article-punching step can create the state wherein the individual support bodies 7 are fixed to the individual forming sheets 3 at the peripheries of the individual microneedle sheets 5. Thereby, the individual microneedle sheets 5 are protected from outside contamination.

Thus, in the state in which the microneedle sheet packaging body 1 has been completed, the microneedle sheet 5 is fixed to the forming sheet 3 by the support body 7 and the adhesive layer 9. In so doing, the microneedles 11 are protected when the microneedle sheet packaging body 1 is transported or used.

As discussed above, the forming sheet 3 functions as a forming die for forming the microneedles 11 of the microneedle sheet 5. In addition, the forming sheet 3 functions as a protective material that protects the microneedles 11 of each microneedle sheet 5.

2. Second Embodiment

In the abovementioned first embodiment, the outer-circumference-side portion farther on the outer side of the outer circumferential edge of the microneedle sheet 5 is entirely enclosed by the structure wherein the support body 7 is fixed to the upper surface of the forming sheet 3 via the adhesive layer 9. However, the present invention is not limited to the abovementioned structure. Other structures of the outer-circumference-side portion of the microneedle sheet 5 are explained below.

An example in which the microneedle sheet is made into a tabbed shape is explained below.

Figure 24:
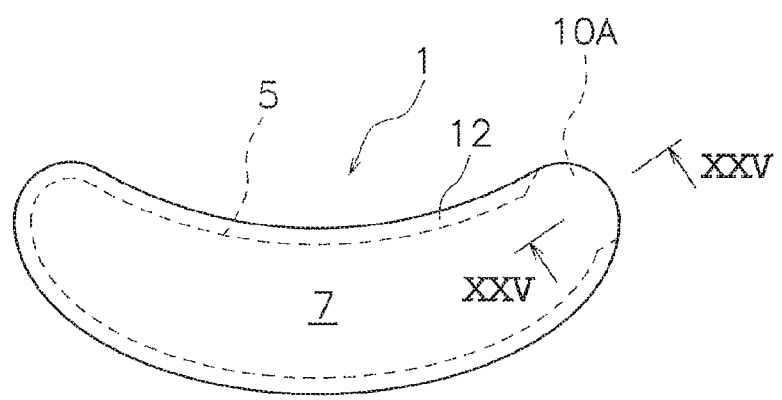
FIG. 24 is a plan view of the microneedle-sheet packaging body according to a second embodiment of the present invention.
Figure 25:
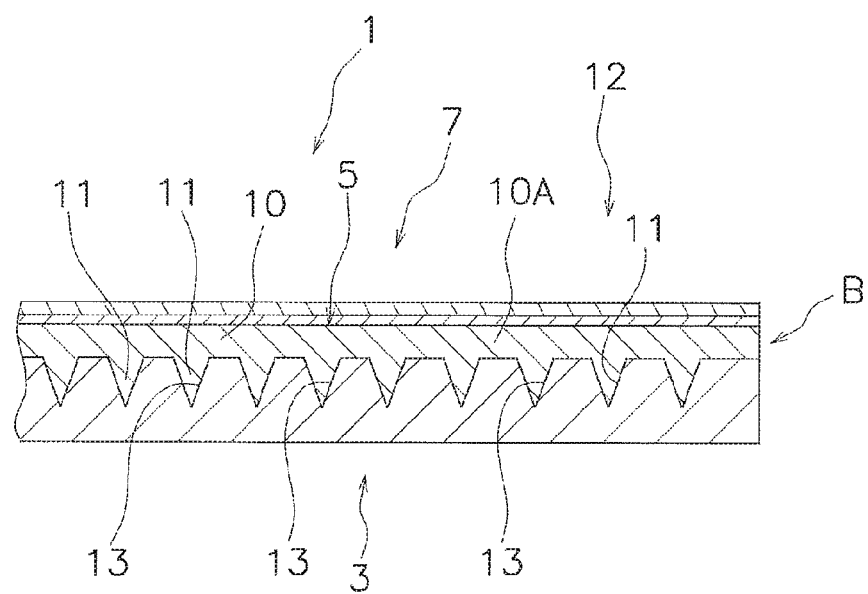
FIG. 25 is a cross-sectional view taken along line XXV-XXV in FIG. 24 and is a cross-sectional view of the microneedle-sheet packaging body.

As shown in FIG. 24 and FIG. 25, the microneedle sheet 5 includes a projecting part 10A that extends from the substrate 10 in the sheet-surface direction and is interposed between the support body 7 and the forming sheet 3. FIG. 24 is a plan view of the microneedle-sheet packaging body according to the second embodiment of the present invention. FIG. 25 is a cross-sectional view taken along line XXV-XXV in FIG. 24 and is a cross-sectional view of the microneedle-sheet packaging body.

Specifically, in this packaging body, the support body 7 (i.e., the adhesive layer 9) does not contact the forming sheet 3 at the location of the projecting part 10A of the microneedle sheet 5, and therefore the bonding strength between the forming sheet 3 and other members is low at that portion of the outer-perimeter part 12. Accordingly, the support body 7 can be easily peeled from the forming sheet 3 by holding and pulling, by hand, an edge (refer to arrow B) of the projecting part 10A of the microneedle sheet 5. In particular, because the microneedle sheet 5 can be directly grasped, the microneedle sheet 5 is reliably peeled from the forming sheet 3.

3. Shared Features of the Embodiments

The first and second embodiments have the following points in common.

The microneedle-sheet packaging body (e.g., the packaging body 1) includes the microneedle sheet (e.g., the microneedle sheet 5), the sheet member (e.g., the forming sheet 3), and the support-base-material sheet (e.g., the support body 7). The microneedle sheet includes the main body (e.g., the substrate 10), and the plurality of microneedles (e.g., the microneedles 11) formed on the first surface (e.g., the lower surface) of the main body. The sheet member is tightly adhered to the first surface of the main body. The sheet member includes the plurality of micro-recess parts (e.g., the micro-recess parts 13) in which the plurality of microneedles is housed. The support-base-material sheet is fixed to the second surface (e.g., the upper surface) of the main body of the microneedle sheet and is further fixed to the sheet member around the main body.

In this packaging body, the microneedle sheet is formed in the sheet member (e.g., refer to FIG. 14), and the state at the time when the microneedle sheet was formed is maintained. Specifically, the plurality of microneedles of the microneedle sheet are formed by the plurality of micro-recess parts of the sheet member and are also subsequently protected by the plurality of micro-recess parts. That is, the plurality of microneedles of the microneedle sheet are reliably protected.

In addition, the packaging body includes the sheet-shaped base material, which is fixed to the second surface of the main body of the microneedle sheet and is further fixed to the sheet member around the main body (e.g., refer to FIG. 1), and therefore the microneedle sheet is reliably protected.

4. Other Embodiments

The above explained one embodiment of the present invention, but the present invention is not limited to the abovementioned embodiment, and it is understood that various modifications may be effected without departing from the gist of the invention. In particular, the embodiments and modified examples written in the present specification can be arbitrarily combined as needed.

(a) In the abovementioned embodiments, the cutting of the various sheets is performed by a trimming die but may be performed by some other means such as a laser.

(b) In the abovementioned embodiments, the number of the housing parts of the microneedle-sheet packaging body is one, but there may be a plurality of housing parts.

The present invention can be broadly applied to a microneedle-sheet packaging body including a plurality of microneedles and to a method of manufacturing the same.

The invention claimed is:

1. A microneedle-sheet packaging body comprising:
   a sheet member formed with a plurality of micro-recess parts over an entire surface thereof;
   a microneedle sheet including a sheet-shaped main body and a plurality of microneedles formed on a first surface of the main body, the microneedle sheet allowing the micro-recess parts to be exposed around the sheet member and being tightly adhered to the sheet member such that the plurality of microneedles are housed in the plurality of micro-recess parts; and
   a sheet-shaped base material fixed to the sheet member over an entire surface thereof such that the sheet-shaped base material covers the microneedle sheet and makes contact with portions of the sheet member where the micro-recess parts are exposed around the microneedle sheet.

2. The microneedle-sheet packaging body according to claim 1, wherein
   a part of the microneedle sheet extends up to an outer circumferential edge of the sheet-shaped base material.

3. The microneedle-sheet packaging body according to claim 2, further comprising:
   an adhesive fixed to a surface of the sheet-shaped base material on the sheet member side, the adhesive being adhered to a second surface of the main body of the microneedle sheet, and being further adhered to the sheet member around the main body.

4. The microneedle-sheet packaging body according to claim 3, wherein
   the peel strength between the sheet-shaped base material and the microneedle sheet is higher than the peel strength between the microneedle sheet and the sheet member.

5. The microneedle-sheet packaging body according to claim 1, further comprising:
   an adhesive fixed to a surface of the sheet-shaped base material on the sheet member side, the adhesive being adhered to a second surface of the main body of the microneedle sheet, and being further adhered to the sheet member around the main body.

6. The microneedle-sheet packaging body according to claim 5, wherein
   the peel strength between the sheet-shaped base material and the microneedle sheet is higher than the peel strength between the microneedle sheet and the sheet member.

7. The microneedle-sheet packaging body according to claim 1, wherein
   the peel strength between the sheet-shaped base material and the microneedle sheet is higher than the peel strength between the microneedle sheet and the sheet member.

8. The microneedle-sheet packaging body according to claim 2, wherein
   the peel strength between the sheet-shaped base material and the microneedle sheet is higher than the peel strength between the microneedle sheet and the sheet member.

9. A method of manufacturing a microneedle-sheet packaging body according to claim 1, the microneedle-sheet packaging body manufacturing method comprising:
   forming the plurality of micro-recess parts on a whole-sheet member over the entire surface thereof;
   supplying a microneedle material to the whole-sheet member such that a whole-microneedle sheet is formed, the whole-microneedle sheet including the main body and the plurality of microneedles formed on the first surface of the main body and disposed inside the plurality of micro-recess parts;
   half-cutting the whole-microneedle sheet such that a desired plurality of individual microneedle sheets are formed such that cutting blades do not reach a lower surface of the whole-sheet member, and subsequently eliminating an unnecessary part of the whole-microneedle sheet;
   fixing a whole-sheet-shaped base material to the plurality of individual microneedle sheets entirely such that the whole-sheet-shaped base material covers the plurality of individual microneedle sheets and makes contact with portions where the micro-recess parts of the whole-sheet member are exposed around the individual microneedle sheets; and
   punching, in units of the plurality of individual microneedle sheets, the whole-sheet member and the whole-sheet-shaped base material around each of the individual microneedle sheets such that a plurality of microneedle-sheet packaging bodies are formed, each microneedle-sheet packaging body having the individual microneedle sheet, an individual sheet member, and an individual sheet-shaped base material.

* * * * *